United States Patent
Beard et al.

(10) Patent No.: US 8,729,096 B2
(45) Date of Patent: May 20, 2014

(54) IMIDAZOLIDINE-2,4-DIONE DERIVATIVES AS N-FORMYL PEPTIDE RECEPTOR 2 MODULATORS

(71) Applicant: Allergan, Inc., Irvine, CA (US)

(72) Inventors: Richard L. Beard, Newport Beach, CA (US); Vidyasagar Vuligonda, Irvine, CA (US); John E. Donello, Dana Point, CA (US); Veena Viswanath, Irvine, CA (US); Michael E. Garst, Newport Beach, CA (US)

(73) Assignee: Allergan, Inc., Irvine, CA (US)

( * ) Notice: Subject to any disclaimer, the term of this patent is extended or adjusted under 35 U.S.C. 154(b) by 0 days.

(21) Appl. No.: 13/765,527

(22) Filed: Feb. 12, 2013

(65) Prior Publication Data

US 2013/0217720 A1    Aug. 22, 2013

Related U.S. Application Data

(60) Provisional application No. 61/599,522, filed on Feb. 16, 2012.

(51) Int. Cl.
| | |
|---|---|
| *A61K 31/4353* | (2006.01) |
| *A61K 31/4178* | (2006.01) |
| *A61K 31/4164* | (2006.01) |
| *C07D 471/06* | (2006.01) |
| *C07D 487/10* | (2006.01) |
| *C07D 233/02* | (2006.01) |

(52) U.S. Cl.
CPC ......... *A61K 31/4353* (2013.01); *A61K 31/4178* (2013.01); *A61K 31/4164* (2013.01); *C07D 471/06* (2013.01); *C07D 487/10* (2013.01); *C07D 233/02* (2013.01)
USPC ........... 514/300; 514/387; 514/389; 546/121; 548/301.4; 548/302.7; 548/319.5

(58) Field of Classification Search
CPC ........... A61K 31/4353; A61K 31/4178; A61K 31/4164; C07D 471/06; C07D 487/10; C07D 233/03
USPC ........ 514/300, 387, 389; 546/121; 548/301.4, 548/302.7, 319.5
See application file for complete search history.

(56) References Cited

U.S. PATENT DOCUMENTS 4,521,210 A    6/1985   Wong

FOREIGN PATENT DOCUMENTS

WO    WO2010-134014    11/2010

OTHER PUBLICATIONS

Migeotte, Isabelle, Cytokine & Growth Factor Reviews 17, 2006, pp. 501-519, Elsevier.
Cross, L.C., Pure & Appl.. Chem., vol. 45, pp. 11-30. Pergamon Press, 1976. Printed in Great Britain.
Stahl, Heinrich, Handbook of Pharmaceutical Salts, Verlag Helvetica Chemica Acta—Zürich, 2002, 329-345.
Dufton, Neil et al., Pharmacology & Therapeutics 127, 2010, pp. 175-188, Elsevier, United Kingdom.
International Search Report, PCT/US2013/025770, Apr. 15, 2013.

*Primary Examiner* — Samantha Shterengarts
(74) *Attorney, Agent, or Firm* — Doina G. Ene

(57) ABSTRACT

The present invention relates to novel imidazolidine-2,4-dione derivatives, processes for preparing them, pharmaceutical compositions containing them and their use as pharmaceuticals as modulators of the N-formyl peptide receptor 2 (FPR2).

14 Claims, No Drawings

IMIDAZOLIDINE-2,4-DIONE DERIVATIVES AS N-FORMYL PEPTIDE RECEPTOR 2 MODULATORS

CROSS REFERENCE TO RELATED APPLICATION

This application claims the benefit of U.S. Provisional Application Ser. No. 61/599,522, filed Feb. 16, 2012, the disclosure of which is hereby incorporated in its entirety herein by reference.

FIELD OF THE INVENTION

The present invention relates to novel imidazolidine-2,4-dione derivatives, processes for preparing them, pharmaceutical compositions containing them and their use as pharmaceuticals, as modulators of the N-formyl peptide receptor 2 (FPR2). The invention relates specifically to the use of these compounds and their pharmaceutical compositions to treat disorders associated with the N-formyl peptide receptor 2 modulation.

BACKGROUND OF THE INVENTION

The N-formyl peptide receptor 2 (FPR2), also known as N-formyl peptide receptor like-1 (FPRL-1), is a G protein-coupled receptor that is expressed on inflammatory cells such as monocytes and neutrophils, as well as in T cells and has been shown to play a critical role in leukocyte trafficking during inflammation and human pathology. FPR2 is an exceptionally promiscuous receptor that responds to a large array of exogenous and endogenous ligands, including Serum amyloid A (SAA), chemokine variant sCKβ8-1, the neuroprotective peptide, anti-inflammatory eicosanoid lipoxin A4 (LXA4) and glucocotricoid-modulated protein annexin A1. FPR2 transduces anti-inflammatory effects of LXA4 in many systems, but it can also mediate the pro-inflammatory signaling cascade of peptides such as SAA. The ability of the receptor to mediate two opposite effects is proposed to be a result of different receptor domains used by different agonists (Parmentier, Marc et al. Cytokine & Growth Factor Reviews 17 (2006) 501-519).

Activation of FPR2 by lipoxin A4 or its analogs and by Annexin I protein has been shown to result in anti-inflammatory activity by promoting active resolution of inflammation which involves inhibition of polymorphonuclear neutrophils (PMNs) and eosinophils migration and also stimulate monocyte migration enabling clearance of apoptotic cells from the site of inflammation in a nonphlogistic manner. In addition, FPR2 has been shown to inhibit NK cytotoxicity and promote activation of T cells which further contributes to down regulation of tissue damaging inflammatory signals. FPR2/LXA4 interaction has been shown to be beneficial in experimental models of ischemia reperfusion, angiogenesis, dermal inflammation, chemotherapy-induced alopecia, ocular inflammation such as but not limited to: endotoxin-induced uveitis, corneal wound healing, re-epithelialization. FPR2 thus represents an important novel pro-resolutionary molecular target for the development of new therapeutic agents in diseases with excessive inflammatory responses.

SUMMARY OF THE INVENTION

A group of novel imidazolidine-2,4-dione derivatives which are potent and selective FPR2 modulators has been discovered. As such, the compounds described herein are useful in treating a wide variety of disorders associated with modulation of FPR2 receptor. The term "modulator" as used herein, includes but is not limited to: receptor agonist, antagonist, inverse agonist, inverse antagonist, partial agonist, partial antagonist.

This invention describes compounds of Formula I, which have FPR2 receptor biological activity. The compounds in accordance with the present invention are thus of use in medicine, for example in the treatment of humans with diseases and conditions that are alleviated by FPR2 receptor modulation.

In one aspect, the invention provides a compound represented by Formula I or a pharmaceutically acceptable salt thereof or the individual enantiomers, diastereoisomers, zwitterions, tautomers or pharmaceutically acceptable salts thereof:

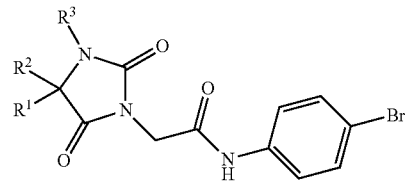

Formula I wherein:

$R^1$ is hydrogen, halogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted $C_{3-8}$ cycloalkyl, substituted or unsubstituted $C_{3-8}$ cycloalkenyl substituted or unsubstituted heterocycle or substituted or unsubstituted $C_{6-10}$ aryl, or together with $R^2$ can form an optionally substituted cyclobutyl;

$R^2$ is isopropyl or together with $R^3$ can form a substituted or unsubstituted 3 to 6 member ring heterocycle or together with $R^1$ can form an optionally substituted cyclobutyl, cyclopropyl;

$R^3$ is hydrogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted $C_{3-8}$ cycloalkyl, substituted or unsubstituted $C_{3-8}$ cycloalkenyl, substituted or unsubstituted heterocycle, substituted or unsubstituted $C_{6-10}$ aryl or together with $R^2$ can form a substituted or unsubstituted 3 to 6 member ring heterocycle; and compounds N-(4-Bromophenyl)-2-(4,4-diethyl-2,5-dioxoimidazolidin-1-yl)propanamide;

N-(4-Bromophenyl)-2-(4-methoxymethyl)-4-methyl-2,5-dioxoimidazolidin-1-yl)acetamide; and, N-(4-Bromophenyl)-2-(4,4-dimethyl-2,5-dioxoimidazolidin-1-yl)propanamide.

In another aspect, the invention provides a compound having Formula I wherein:

$R^1$ is hydrogen, halogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted $C_{3-8}$ cycloalkyl, substituted or unsubstituted $C_{3-8}$ cycloalkenyl substituted or unsubstituted heterocycle or substituted or unsubstituted $C_{6-10}$ aryl; and, $R^2$ and $R^3$ form a substituted or unsubstituted 3 to 6 member ring heterocycle.

In another aspect, the invention provides a compound having Formula I wherein:
$R^1$ is hydrogen; and,
$R^2$ and $R^3$ form a substituted or unsubstituted 3 to 6 member ring heterocycle.

In another aspect, the invention provides a compound having Formula I wherein:
$R^1$ together with $R^2$ forms an optionally substituted cyclobutyl or cyclopropyl; and, $R^3$ is hydrogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted $C_{3-8}$ cycloalkyl, substituted or unsubstituted $C_{3-8}$ cycloalkenyl, substituted or unsubstituted heterocycle, substituted or unsubstituted $C_{6-10}$ aryl.

In another aspect, the invention provides a compound having Formula I wherein:
$R^1$ together with $R^2$ forms an optionally substituted cyclobutyl; and, $R^3$ is hydrogen or substituted or unsubstituted $C_{1-6}$ alkyl.

In another aspect, the invention provides a compound having Formula I wherein:
$R^1$ is hydrogen, halogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted $C_{3-8}$ cycloalkyl, substituted or unsubstituted $C_{3-8}$ cycloalkenyl substituted or unsubstituted heterocycle or substituted or unsubstituted $C_{6-10}$ aryl;
$R^2$ is isopropyl; and,
$R^3$ is H, substituted or unsubstituted $C_{1-6}$ alkyl, substituted or unsubstituted $C_{2-6}$ alkenyl, substituted or unsubstituted $C_{2-6}$ alkynyl, substituted or unsubstituted $C_{3-8}$ cycloalkyl, substituted or unsubstituted $C_{3-8}$ cycloalkenyl, substituted or unsubstituted heterocycle, substituted or unsubstituted $C_{6-10}$ aryl.

In another aspect, the invention provides a compound having Formula I wherein:
$R^1$ is substituted or unsubstituted $C_{1-6}$ alkyl;
$R^2$ is isopropyl; and,
$R^3$ is hydrogen.

The term "alkyl", as used herein, refers to saturated, monovalent or divalent hydrocarbon moieties having linear or branched moieties or combinations thereof and containing 1 to 6 carbon atoms, unless otherwise specified. One methylene (—CH$_2$—) group, of the alkyl can be replaced by oxygen, sulfur, sulfoxide, nitrogen, —NH—, carbonyl, carboxyl, sulfonyl, amido, sulfonamido, by a divalent $C_{3-6}$ cycloalkyl, by a divalent heterocycle, or by a divalent aryl group. Alkyl groups can be independently substituted by halogen, hydroxyl, cycloalkyl, amine, heterocyclic, carboxylic acid, —C$_{2-6}$ alkenyl, —C$_{2-6}$ alkynyl, phosphonic acid, phosphonate, sulphonic acid, sulfonate, sulfate, phosphoric acid, nitro, amide, sulfonamides, ketone, aldehydes or esters groups.

The term "halogen", as used herein, refers to an atom of chlorine, bromine, fluorine, iodine.

The term "cycloalkyl", as used herein, refers to a monovalent or divalent group of 3 to 8 carbon atoms derived from a saturated cyclic hydrocarbon. Cycloalkyl groups can be monocyclic or polycyclic. Cycloalkyl can be independently substituted by halogen, —SC$_{1-6}$ alkyl, —S(O)$_2$C$_{1-6}$ alkyl, —S(O)C$_{1-6}$ alkyl, sulfonamide, amide, nitro, cyano, —O(C$_{1-6}$ alkyl), —C$_{1-6}$ alkyl, —C$_{2-6}$ alkenyl, —C$_{2-6}$ alkynyl, ketone, amine, C$_{3-8}$ cycloalkyl, aldehyde, esters, ketone, carboxylic acid, phosphonic acid, sulfonic acid or hydroxyl groups.

The term "cycloalkenyl", as used herein, refers to a monovalent or divalent group of 3 to 8 carbon atoms derived from a saturated cycloalkyl having at least one double bond. Cycloalkenyl groups can be monocyclic or polycyclic. Cycloalkenyl groups can be independently substituted by halogen, —SC$_{1-6}$ alkyl, —S(O)$_2$C$_{1-6}$ alkyl, —S(O)C$_{1-6}$ alkyl, sulfonamide, amide, nitro, cyano, —O(C$_{1-6}$ alkyl), —C$_{1-6}$ alkyl, —O$_{2-6}$ alkenyl, —C$_{2-6}$ alkynyl, ketone, amine, C$_{3-8}$ cycloalkyl, aldehyde, ester, carboxylic acid, phosphonic acid, sulfonic acid or hydroxyl groups.

The term "aryl" as used herein, refers to an organic moiety derived from an aromatic hydrocarbon consisting of a ring containing 6 to 10 carbon atoms by removal of one hydrogen, which can be substituted by halogen, —SO$_{1-6}$ alkyl, —S(O)$_2$ C$_{1-6}$ alkyl, —S(O)C$_{1-6}$ alkyl, sulfonamide, amide, nitro, cyano, —OC$_{1-6}$ alkyl, —C$_{1-6}$ alkyl, —O$_{2-6}$ alkenyl, —C$_{2-6}$ alkynyl, ketone, amine, C$_{3-8}$ cycloalkyl, aldehyde, ester, carboxylic acid, phosphonic acid, sulfonic acid or hydroxyl groups.

The term "heterocycle" as used herein, refers to a 3 to 10 membered ring, which can be aromatic or non-aromatic, saturated or unsaturated, containing at least one heteroatom selected form O or N or S or combinations of at least two thereof, interrupting the carbocyclic ring structure. The heterocyclic ring can be saturated or unsaturated. The heterocyclic ring can be interrupted by a C=O; the S and N heteroatoms can be oxidized. Heterocycles can be monocyclic or polycyclic. Heterocyclic ring moieties can be substituted by halogen, —SC$_{1-6}$ alkyl, —S(O)$_2$C$_{1-6}$ alkyl, —S(O)C$_{1-6}$ alkyl, sulfonamide, amide, nitro, cyano, —OC$_{1-6}$ alkyl, —C$_{1-6}$ alkyl, —C$_{2-6}$ alkenyl, —C$_{2-6}$ alkynyl, ketone, amine, C$_{3-8}$ cycloalkyl, aldehydes, esters, carboxylic acid, phosphonic acid, sulfonic acid or hydroxyl groups.

The term "hydroxyl" as used herein, represents a group of formula "—OH".

The term "carbonyl" as used herein, represents a group of formula "—C(O)—".

The term "aldehyde" as used herein, represents a group of formula "—C(O)H".

The term "ketone" as used herein, represents a group of formula —C(O)R$^x$ wherein R$^x$ can be alkyl, aryl, cycloalkyl, cycloalkenyl, or heterocycle as defined above.

The term "ester" as used herein, represents a group of formula —C(O)OR$^x$ wherein R$^x$ can be alkyl, aryl, cycloalkyl, cycloalkenyl, or heterocycle as defined above.

The term "amine" as used herein, represents a group of formula NR$^x$R$^y$," wherein R$^x$ and R$^y$ can be independently hydrogen, alkyl, aryl, cycloalkyl, cycloalkenyl, or heterocycle as defined above.

The term "carboxyl" as used herein, represents a group of formula "—C(O)O—".

The term "sulfonyl" as used herein, represents a group of formula "—SO$_2$—".

The term "sulfate" as used herein, represents a group of formula "—O—S(O)$_2$—O—".

The term "sulfonate" as used herein, represents a group of the formula "—S(O)$_2$—OR$^x$—," wherein Rx can be hydrogen, alkyl, aryl, cycloalkyl, cycloalkenyl, heterocycle as defined above.

The term "carboxylic acid" as used herein, represents a group of formula "—C(O)OH".

The term "nitro" as used herein, represents a group of formula "—NO$_2$".

The term "cyano" as used herein, represents a group of formula "—CN".

The term "amide" as used herein, represents a group of formula "—C(O)NR$^x$R$^y$," wherein R$^x$ and R$^y$ can be independently hydrogen, alkyl, aryl, cycloalkyl, cycloalkenyl, heterocycle as defined above.

The term "amido" as used herein, represents a group of formula "—C(O)NR$^x$—," wherein R$^x$ can be hydrogen, alkyl, aryl, cycloalkyl, cycloalkenyl, heterocycle as defined above.

The term "sulfonamide" as used herein, represents a group of formula "—S(O)$_2$NR$^x$R$^y$" wherein R$^x$ and R$^y$ can independently be hydrogen, alkyl, aryl, cycloalkyl, cycloalkenyl, heterocycle as defined above.

The term "sulfonamido" as used herein, represents a group of formula "—S(O)$_2$NR$^x$—" wherein R$^x$ can be hydrogen, alkyl, aryl, cycloalkyl, cycloalkenyl, heterocycle as defined above.

The term "sulfoxide" as used herein, represents a group of formula "—S(O)—". The term "phosphonic acid" as used herein, represents a group of formula "—P(O)(OH)$_2$".

The term "phosphonate" as used herein, represents a group of formula "—P(O)(OR$^x$)(OR$^y$)," wherein R$^x$ and R$^y$ can be independently hydrogen, alkyl, aryl, cycloalkyl, cycloalkenyl, heterocycle as defined above.

The term "phosphoric acid" as used herein, represents a group of formula "—OP(O)(OH)$_2$".

The term "sulphonic acid" as used herein, represents a group of formula "—S(O)$_2$OH".

The formula "H", as used herein, represents a hydrogen atom.

The formula "O", as used herein, represents an oxygen atom.

The formula "N", as used herein, represents a nitrogen atom.

The formula "S", as used herein, represents a sulfur atom.

Compounds of the invention are:
N-(4-bromophenyl)-2-(4-ethyl-4-isopropyl-2,5-dioxoimidazolidin-1-yl)acetamide;
N-(4-bromophenyl)-2-(1,3-dioxotetrahydro-1H-pyrrolo[1,2-c]imidazol-2(3H)-yl)acetamide;
N-(4-bromophenyl)-2-(1,3-dioxohexahydroimidazo[1,5-a]pyridin-2(3H)-yl)acetamide;
N-(4-Bromophenyl)-2-(4,4-diethyl-2,5-dioxoimidazolidin-1-yl)propanamide;
N-(4-Bromophenyl)-2-(4-methoxymethyl)-4-methyl-2,5-dioxoimidazolidin-1-yl)acetamide;
N-(4-Bromophenyl)-2-(6,8-dioxo-5,7-diazaspiro[3.4]octan-7-yl)acetamide;
N-(4-Bromophenyl)-2-(4,4-dimethyl-2,5-dioxoimidazolidin-1-yl)propanamide.

Some compounds of the invention and some of their intermediates have at least one asymmetric center in their structure. This asymmetric center may be present in an R or S configuration, said R and S notation is used in correspondence with the rules described in Pure Appli. Chem. (1976), 45, 11-13.

The term "pharmaceutically acceptable salts" refers to salts or complexes that retain the desired biological activity of the above identified compounds and exhibit minimal or no undesired toxicological effects. The "pharmaceutically acceptable salts" according to the invention include therapeutically active, non-toxic base or acid salt forms, which the compounds of the invention are able to form.

The acid addition salt form of a compound of the invention that occurs in its free form as a base can be obtained by treating the free base with an appropriate acid such as an inorganic acid, for example, hydrochloric acid, hydrobromic acid, sulfuric acid, phosphoric acid, nitric acid and the like; or an organic acid such as for example, acetic acid, hydroxyacetic acid, propanoic acid, lactic acid, pyruvic acid, malonic acid, fumaric acid, maleic acid, oxalic acid, tartaric acid, succinic acid, malic acid, ascorbic acid, benzoic acid, tannic acid, pamoic acid, citric acid, methylsulfonic acid, ethanesulfonic acid, benzenesulfonic acid, formic and the like (Handbook of Pharmaceutical Salts, P. Heinrich Stahal& Camille G. Wermuth (Eds), Verlag Helvetica Chemica Acta—Zürich, 2002, 329-345).

The base addition salt form of a compound of the invention that occurs in its acid form can be obtained by treating the acid with an appropriate base such as an inorganic base, for example, sodium hydroxide, magnesium hydroxide, potassium hydroxide, calcium hydroxide, ammonia and the like; or an organic base such as for example, L-Arginine, ethanolamine, betaine, benzathine, morpholine and the like. (Handbook of Pharmaceutical Salts, P. Heinrich Stahl& Camille G. Wermuth (Eds), Verlag Helvetica Chemica Acta—Zürich, 2002, 329-345).

Compounds of the invention and their salts can be in the form of a solvate, which is included within the scope of the present invention. Such solvates include for example hydrates, alcoholates and the like.

With respect to the present invention reference to a compound or compounds, is intended to encompass that compound in each of its possible isomeric forms and mixtures thereof unless the particular isomeric form is referred to specifically.

Compounds according to the present invention may exist in different polymorphic forms. Although not explicitly indicated in the above formula, such forms are intended to be included within the scope of the present invention.

The compounds of the invention are indicated for use in treating or preventing conditions in which there is likely to be a component involving the N-formyl peptide receptor 2.

In another embodiment, there are provided pharmaceutical compositions including at least one compound of the invention in a pharmaceutically acceptable carrier.

In a further embodiment of the invention, there are provided methods for treating disorders associated with modulation of the N-formyl peptide receptor 2.

Such methods can be performed, for example, by administering to a subject in need thereof a pharmaceutical composition containing a therapeutically effective amount of at least one compound of the invention.

Therapeutic utilities of the N-formyl peptide receptor 2 modulators are ocular inflammatory diseases including, but not limited to, wet and dry age-related macular degeneration (ARMD), uveitis, dry eye, Keratitis, allergic eye disease and conditions affecting the posterior part of the eye, such as maculopathies and retinal degeneration including non-exudative age related macular degeneration, exudative age related macular degeneration, choroidal neovascularization, diabetic retinopathy (proliferative), retinopathy of prematurity (ROP), acute macular neuroretinopathy, central serous chorioretinopathy, cystoid macular edema, and diabetic macular edema, infectious keratitis, post-surgery corneal wound healing, herpetic keratitis, corneal angiogenesis, lymphangiogenesis, retinitis, choroiditis, acute multifocal placoid pigment epitheliopathy, Behcet's disease, birdshot retinochoroidopathy, infectious (syphilis, lyme, tuberculosis, toxoplasmosis), intermediate uveitis (pars planitis), multifocal choroiditis, multiple evanescent white dot syndrome (mewds), ocular sarcoidosis, posterior scleritis, serpiginous choroiditis, subretinal fibrosis, uveitis syndrome, Vogt-Koyanagi- and Harada syndrome, vascular diseases, vascular exudative diseases, retinal arterial occlusive disease, central retinal vein occlusion, cystoids macular edema, disseminated intravascular coagulopathy, branch retinal vein occlusion, hypertensive fundus changes, ocular ischemic syndrome, retinal arterial microaneurysms, Coat's disease, parafoveal telangiectasis, hemi-retinal vein occlusion, papillophlebitis, central retinal artery occlusion, branch retinal artery occlusion, carotid artery disease (CAD), frosted branch angiitis, sickle cell retinopathy, hemoglobinopathies, angioid streaks, familial exudative vitreoretinopathy, Eales disease, traumatic and surgical conditions, sympathetic ophthalmia, uveitic retinal disease, corneal wound healing, retinal detachment, trauma, conditions caused by laser, conditions caused by photodynamic therapy, photocoagulation, hypoperfusion during surgery, radiation retinopathy, bone marrow transplant retinopathy, proliferative disorders, proliferative vitreal retinopathy and epiretinal membranes, proliferative diabetic retinopathy, infectious disorders, ocular histoplasmosis, ocular toxocariasis, presumed ocular histoplasmosis syndrome (PONS), endophthalmitis, toxoplasmosis, retinal diseases associated with HIV infection, choroidal disease associated with HIV infection, uveitic disease associated with HIV infection, viral retinitis, acute retinal necrosis, progressive outer retinal necrosis, fungal retinal diseases, ocular syphilis, ocular tuberculosis, diffuse unilateral subacute neuroretinitis, myiasis, genetic disorders, retinitis pigmentosa, systemic disorders associated with retinal dystrophies, congenital stationary night blindness, cone dystrophies, Stargardt's disease, fundus flavimaculatus, Best's disease, pattern dystrophy of the retinal pigmented epithelium, X-linked retinoschisis, Sorsby's fundus dystrophy, benign concentric maculopathy, Bietti's crystalline dystrophy, pseudoxanthoma elasticum; retinal tears and holes such as retinal detachment, macular hole, giant retinal tear, tumors such as retinal disease associated with tumors, congenital hypertrophy of the retinal pigmented epithelium, posterior uveal melanoma, choroidal hemangioma, choroidal osteoma, choroidal metastasis, combined hamartoma of the retina and retinal pigmented epithelium, retinoblastoma, vasoproliferative tumors of the ocular fundus, retinal astrocytoma, and intraocular lymphoid tumors, miscellaneous diseases affecting the posterior part of the eye such as punctate inner choroidopathy, acute posterior multifocal placoid pigment epitheliopathy, myopic retinal degeneration, and acute retinal pigment epitheliitis, systemic inflammatory diseases such as stroke, coronary artery disease, obstructive airway diseases, HIV-mediated retroviral infections, cardiovascular disorders including coronary artery disease, neuroinflammation, neurological disorders, pain and immunological disorders, asthma, allergic disorders, inflammation, systemic lupus erythematosus, psoriasis, CNS disorders such as Alzheimer's disease, arthritis, sepsis, inflammatory bowel disease, cachexia, angina pectoris, post-surgical corneal inflammation, blepharitis, MGD, dermal wound healing, burns, rosacea, atopic dermatitis, acne, psoriasis, seborrheic dermatitis, actinic keratoses, viral warts, photoaging, rheumatoid arthritis, related inflammatory disorders, alopecia, glaucoma, branch vein occlusion, Best's vitelliform macular degeneration, retinitis pigmentosa, proliferative vitreoretinopathy (PVR), and any other degenerative disease of either the photoreceptors or the RPE (Perretti, Mauro et al. Pharmacology & Therapeutics 127 (2010) 175-188.)

These compounds are useful for the treatment of mammals, including humans, with a range of conditions and diseases that are alleviated by the N-formyl peptide receptor 2 modulation: including, but not limited to the treatment of ocular inflammatory diseases: wet and dry age-related macular degeneration (ARMD), uveitis, dry eye, Keratitis, allergic eye disease and conditions affecting the posterior part of the eye, such as maculopathies and retinal degeneration including non-exudative age related macular degeneration, exudative age related macular degeneration, choroidal neovascularization, diabetic retinopathy (proliferative), retinopathy of prematurity (ROP), acute macular neuroretinopathy, central serous chorioretinopathy, cystoid macular edema, and diabetic macular edema, infectious keratitis, post-surgery corneal wound healing, herpetic keratitis, corneal angiogenesis, lymphangiogenesis, retinitis, choroiditis, acute multifocal placoid pigment epitheliopathy, Behcet's disease, birdshot retinochoroidopathy, infectious (syphilis, lyme, tuberculosis, toxoplasmosis), intermediate uveitis (pars planitis), multifocal choroiditis, multiple evanescent white dot syndrome (mewds), ocular sarcoidosis, posterior scleritis, serpiginous choroiditis, subretinal fibrosis, uveitis syndrome, Vogt-Koyanagi- and Harada syndrome, vascular diseases, vascular exudative diseases, retinal arterial occlusive disease, central retinal vein occlusion, cystoids macular edema, disseminated intravascular coagulopathy, branch retinal vein occlusion, hypertensive fundus changes, ocular ischemic syndrome, retinal arterial microaneurysms, Coat's disease, parafoveal telangiectasis, hemi-retinal vein occlusion, papillophlebitis, central retinal artery occlusion, branch retinal artery occlusion, carotid artery disease (CAD), frosted branch angiitis, sickle cell retinopathy, hemoglobinopathies, angioid streaks, familial exudative vitreoretinopathy, Eales disease, traumatic and surgical conditions, sympathetic ophthalmia, uveitic retinal disease, corneal wound healing, retinal detachment, trauma, conditions caused by laser, conditions caused by photodynamic therapy, photocoagulation, hypoperfusion during surgery, radiation retinopathy, bone marrow transplant retinopathy, proliferative disorders, proliferative vitreal retinopathy and epiretinal membranes, proliferative diabetic retinopathy, infectious disorders, ocular histoplasmosis, ocular toxocariasis, presumed ocular histoplasmosis syndrome (PONS), endophthalmitis, toxoplasmosis, retinal diseases associated with HIV infection, choroidal disease associated with HIV infection, uveitic disease associated with HIV infection, viral retinitis, acute retinal necrosis, progressive outer retinal necrosis, fungal retinal diseases, ocular syphilis, ocular tuberculosis, diffuse unilateral subacute neuroretinitis, myiasis, genetic disorders, retinitis pigmentosa, systemic disorders associated with retinal dystrophies, congenital stationary night blindness, cone dystrophies, Stargardt's disease, fundus flavimaculatus, Best's disease, pattern dystrophy of the retinal pigmented epithelium, X-linked retinoschisis, Sorsby's fundus dystrophy, benign concentric maculopathy, Bietti's crystalline dystrophy, pseudoxanthoma elasticum; retinal tears and holes such as retinal detachment, macular hole, giant retinal tear, tumors such as retinal disease associated with tumors, congenital hypertrophy of the retinal pigmented epithelium, posterior uveal melanoma, choroidal hemangioma, choroidal osteoma, choroidal metastasis, combined hamartoma of the retina and retinal pigmented epithelium, retinoblastoma, vasoproliferative tumors of the ocular fundus, retinal astrocytoma, and intraocular lymphoid tumors, miscellaneous diseases affecting the posterior part of the eye such as punctate inner choroidopathy, acute posterior multifocal placoid pigment epitheliopathy, myopic retinal degeneration, and acute retinal pigment epitheliitis, systemic inflammatory diseases such as stroke, coronary artery disease, obstructive airway diseases, HIV-mediated retroviral infections, cardiovascular disorders including coronary artery disease, neuroinflammation, neurological disorders, pain and immunological disorders, asthma, allergic disorders, inflammation, systemic lupus erythematosus, psoriasis, CNS disorders such as Alzheimer's disease, arthritis, sepsis, inflammatory bowel disease, cachexia, angina pectoris, post-surgical corneal inflammation, blepharitis, MGD, dermal wound healing, burns, rosacea, atopic dermatitis, acne, psoriasis, seborrheic dermatitis, actinic keratoses, viral warts, photoaging, rheumatoid arthritis, related inflammatory disorders, alopecia, glaucoma, branch vein occlusion, Best's vitelliform macular degeneration, retinitis pigmentosa, proliferative vitreoretinopathy (PVR), and any other degenerative disease of either the photoreceptors or the RPE.

In still another embodiment of the invention, there are provided methods for treating disorders associated with modulation of the FPR2 receptor. Such methods can be performed, for example, by administering to a subject in need thereof a therapeutically effective amount of at least one compound of the invention, or any combination thereof, or pharmaceutically acceptable salts, hydrates, solvates, crystal forms, enantiomers, and diastereomers thereof.

The present invention concerns the use of a compound of the invention or a pharmaceutically acceptable salt thereof, for the manufacture of a medicament for the treatment of ocular inflammatory diseases including, but not limited to, wet and dry age-related macular degeneration (ARMD), uveitis, dry eye, Keratitis, allergic eye disease and conditions affecting the posterior part of the eye, such as maculopathies and retinal degeneration including non-exudative age related macular degeneration, exudative age related macular degeneration, choroidal neovascularization, diabetic retinopathy (proliferative), retinopathy of prematurity (ROP), acute macular neuroretinopathy, central serous chorioretinopathy, cystoid macular edema, and diabetic macular edema, infectious keratitis, post-surgery corneal wound healing, herpetic keratitis, corneal angiogenesis, lymphangiogenesis, retinitis, choroiditis, acute multifocal placoid pigment epitheliopathy, Behcet's disease, birdshot retinochoroidopathy, infectious (syphilis, lyme, tuberculosis, toxoplasmosis), intermediate uveitis (pars planitis), multifocal choroiditis, multiple evanescent white dot syndrome (mewds), ocular sarcoidosis, posterior scleritis, serpiginous choroiditis, subretinal fibrosis, uveitis syndrome, Vogt-Koyanagi- and Harada syndrome, vascular diseases, vascular exudative diseases, retinal arterial occlusive disease, central retinal vein occlusion, cystoids macular edema, disseminated intravascular coagulopathy, branch retinal vein occlusion, hypertensive fundus changes, ocular ischemic syndrome, retinal arterial microaneurysms, Coat's disease, parafoveal telangiectasis, hemi-retinal vein occlusion, papillophlebitis, central retinal artery occlusion, branch retinal artery occlusion, carotid artery disease (CAD), frosted branch angiitis, sickle cell retinopathy, hemoglobinopathies, angioid streaks, familial exudative vitreoretinopathy, Eales disease, traumatic and surgical conditions, sympathetic ophthalmia, uveitic retinal disease, corneal wound healing, retinal detachment, trauma, conditions caused by laser, conditions caused by photodynamic therapy, photocoagulation, hypoperfusion during surgery, radiation retinopathy, bone marrow transplant retinopathy, proliferative disorders, proliferative vitreal retinopathy and epiretinal membranes, proliferative diabetic retinopathy, infectious disorders, ocular histoplasmosis, ocular toxocariasis, presumed ocular histoplasmosis syndrome (PONS), endophthalmitis, toxoplasmosis, retinal diseases associated with HIV infection, choroidal disease associated with HIV infection, uveitic disease associated with HIV infection, viral retinitis, acute retinal necrosis, progressive outer retinal necrosis, fungal retinal diseases, ocular syphilis, ocular tuberculosis, diffuse unilateral subacute neuroretinitis, myiasis, genetic disorders, retinitis pigmentosa, systemic disorders associated with retinal dystrophies, congenital stationary night blindness, cone dystrophies, Stargardt's disease, fundus flavimaculatus, Best's disease, pattern dystrophy of the retinal pigmented epithelium, X-linked retinoschisis, Sorsby's fundus dystrophy, benign concentric maculopathy, Bietti's crystalline dystrophy, pseudoxanthoma elasticum; retinal tears and holes such as retinal detachment, macular hole, giant retinal tear, tumors such as retinal disease associated with tumors, congenital hypertrophy of the retinal pigmented epithelium, posterior uveal melanoma, choroidal hemangioma, choroidal osteoma, choroidal metastasis, combined hamartoma of the retina and retinal pigmented epithelium, retinoblastoma, vasoproliferative tumors of the ocular fundus, retinal astrocytoma, and intraocular lymphoid tumors, miscellaneous diseases affecting the posterior part of the eye such as punctate inner choroidopathy, acute posterior multifocal placoid pigment epitheliopathy, myopic retinal degeneration, and acute retinal pigment epitheliitis, systemic inflammatory diseases such as stroke, coronary artery disease, obstructive airway diseases, HIV-mediated retroviral infections, cardiovascular disorders including coronary artery disease, neuroinflammation, neurological disorders, pain and immunological disorders, asthma, allergic disorders, inflammation, systemic lupus erythematosus, psoriasis, CNS disorders such as Alzheimer's disease, arthritis, sepsis, inflammatory bowel disease, cachexia, angina pectoris, post-surgical corneal inflammation, blepharitis, MGD, dermal wound healing, burns, rosacea, atopic dermatitis, acne, psoriasis, seborrheic dermatitis, actinic keratoses, viral warts, photoaging, rheumatoid arthritis, related inflammatory disorders, alopecia, glaucoma, branch vein occlusion, Best's vitelliform macular degeneration, retinitis pigmentosa, proliferative vitreoretinopathy (PVR), and any other degenerative disease of either the photoreceptors or the RPE. The actual amount of the compound to be administered in any given case will be determined by a physician taking into account the relevant circumstances, such as the severity of the condition, the age and weight of the patient, the patient's general physical condition, the cause of the condition, and the route of administration.

The patient will be administered the compound orally in any acceptable form, such as a tablet, liquid, capsule, powder and the like, or other routes may be desirable or necessary, particularly if the patient suffers from nausea. Such other routes may include, without exception, transdermal, parenteral, subcutaneous, intranasal, via an implant stent, intrathecal, intravitreal, topical to the eye, direct injection, application at the back of the eye or formulations that may further enhance the long duration of actions such as a slow releasing pellet, suspension, gel, or sustained delivery devices such as any suitable drug delivery system (DDS) known in the art. While topical administration is preferred, this compound may also be used in an intraocular implant as described in U.S. Pat. No. 4,521,210 intramuscular, intravenous, and intrarectal modes of delivery. Additionally, the formulations may be designed to delay release of the active compound over a given period of time, or to carefully control the amount of drug released at a given time during the course of therapy.

In another embodiment of the invention, there are provided pharmaceutical compositions including at least one compound of the invention in a pharmaceutically acceptable carrier thereof. The phrase "pharmaceutically acceptable" means the carrier, diluent or excipient must be compatible with the other ingredients of the formulation and not deleterious to the recipient thereof.

Pharmaceutical compositions of the present invention can be used in the form of a solid, a solution, an emulsion, a dispersion, a patch, a micelle, a liposome, and the like, wherein the resulting composition contains one or more compounds of the present invention, as an active ingredient, in admixture with an organic or inorganic carrier or excipient suitable for enteral or parenteral applications. Invention compounds may be combined, for example, with the usual non-toxic, pharmaceutically acceptable carriers for tablets, pellets, capsules, suppositories, solutions, emulsions, suspensions, and any other form suitable for use. The carriers which can be used include glucose, lactose, gum acacia, gelatin, mannitol, starch paste, magnesium trisilicate, talc, corn starch, keratin, colloidal silica, potato starch, urea, medium chain length triglycerides, dextrans, and other carriers suitable for use in manufacturing preparations, in solid, semisolid, or liquid form. In addition auxiliary, stabilizing, thickening and coloring agents and perfumes may be used. Invention compounds are included in the pharmaceutical composition in an amount sufficient to produce the desired effect upon the process or disease condition.

Pharmaceutical compositions containing invention compounds may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known in the art for the manufacture of pharmaceutical compositions and such compositions may contain one or more agents selected from the group consisting of a sweetening agent such as sucrose, lactose, or saccharin, flavoring agents such as peppermint, oil of wintergreen or cherry, coloring agents and preserving agents in order to provide pharmaceutically elegant and palatable preparations. Tablets containing invention compounds in admixture with non-toxic pharmaceutically acceptable excipients may also be manufactured by known methods. The excipients used may be, for example, (1) inert diluents such as calcium carbonate, lactose, calcium phosphate or sodium phosphate; (2) granulating and disintegrating agents such as corn starch, potato starch or alginic acid; (3) binding agents such as gum tragacanth, corn starch, gelatin or acacia, and (4) lubricating agents such as magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed.

In some cases, formulations for oral use may be in the form of hard gelatin capsules wherein the invention compounds are mixed with an inert solid diluent, for example, calcium carbonate, calcium phosphate or kaolin. They may also be in the form of soft gelatin capsules wherein the invention compounds are mixed with water or an oil medium, for example, peanut oil, liquid paraffin or olive oil.

The pharmaceutical compositions may be in the form of a sterile injectable suspension. This suspension may be formulated according to known methods using suitable dispersing or wetting agents and suspending agents. The sterile injectable preparation may also be a sterile injectable solution or suspension in a non-toxic parenterally-acceptable diluent or solvent, for example, as a solution in 1,3-butanediol. Sterile, fixed oils are conventionally employed as a solvent or suspending medium. For this purpose any bland fixed oil may be employed including synthetic mono- or diglycerides, fatty acids (including oleic acid), naturally occurring vegetable oils like sesame oil, coconut oil, peanut oil, cottonseed oil, etc., or synthetic fatty vehicles like ethyl oleate or the like. Buffers, preservatives, antioxidants, and the like can be incorporated as required.

The compounds of the invention may also be administered in the form of suppositories for rectal administration of the drug. These compositions may be prepared by mixing the invention compounds with a suitable non-irritating excipient, such as cocoa butter, synthetic glyceride esters of polyethylene glycols, which are solid at ordinary temperatures, but liquefy and/or dissolve in the rectal cavity to release the drug.

Since individual subjects may present a wide variation in severity of symptoms and each drug has its unique therapeutic characteristics, the precise mode of administration and dosage employed for each subject is left to the discretion of the practitioner.

The compounds and pharmaceutical compositions described herein are useful as medicaments in mammals, including humans, for treatment of diseases and/or alleviations of conditions which are responsive to treatment by agonists or functional antagonists of the N-formyl peptide receptor 2 (FPR2). Thus, in further embodiments of the invention, there are provided methods for treating a disorder associated with modulation of the N-formyl peptide receptor 2 (FPR2). Such methods can be performed, for example, by administering to a subject in need thereof a pharmaceutical composition containing a therapeutically effective amount of at least one invention compound. As used herein, the term "therapeutically effective amount" means the amount of the pharmaceutical composition that will elicit the biological or medical response of a subject in need thereof that is being sought by the researcher, veterinarian, medical doctor or other clinician. In some embodiments, the subject in need thereof is a mammal. In some embodiments, the mammal is human.

The present invention concerns also processes for preparing the compounds of the invention. The compounds according to the invention can be prepared analogously to conventional methods as understood by the person skilled in the art of synthetic organic chemistry. Synthetic Scheme 1 set forth below, illustrates how the compounds according to the invention can be made.

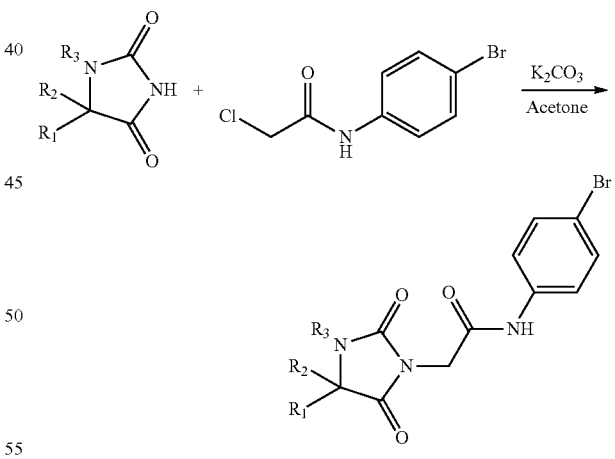

Compounds within the scope of the invention may be prepared as depicted in Scheme 1. In general, a 2,4-Imidazolidinedione, can be reacted with commercially available N-(4-bromophenyl)-2-chloro-acetamide in acetone at room temperature in the presence of potassium carbonate, to provide compounds of the invention. At this stage, those skilled in the art will appreciate that many additional compounds that fall under the scope of the invention may be prepared by performing various common chemical reactions. Details of certain specific chemical transformations are provided in the examples.

DETAILED DESCRIPTION OF THE INVENTION

It is to be understood that both the foregoing general description and the following detailed description are exemplary and explanatory only and are not restrictive of the invention claimed. As used herein, the use of the singular includes the plural unless specifically stated otherwise.

It will be readily apparent to those skilled in the art that some of the compounds of the invention may contain one or more asymmetric centers, such that the compounds may exist in enantiomeric as well as in diastereomeric forms. Unless it is specifically noted otherwise, the scope of the present invention includes all enantiomers, diastereomers and racemic mixtures. Some of the compounds of the invention may form salts with pharmaceutically acceptable acids or bases, and such pharmaceutically acceptable salts of the compounds described herein are also within the scope of the invention.

The present invention includes all pharmaceutically acceptable isotopically enriched compounds. Any compound of the invention may contain one or more isotopic atoms enriched or different than the natural ratio such as deuterium $^2$H (or D) in place of protium $^1$H (or H) or use of $^{13}$C enriched material in place of $^{12}$C and the like. Similar substitutions can be employed for N, O and S. The use of isotopes may assist in analytical as well as therapeutic aspects of the invention. For example, use of deuterium may increase the in vivo half-life by altering the metabolism (rate) of the compounds of the invention. These compounds can be prepared in accord with the preparations described by use of isotopically enriched reagents.

The following examples are for illustrative purposes only and are not intended, nor should they be construed as limiting the invention in any manner. Those skilled in the art will appreciate that variations and modifications of the following examples can be made without exceeding the spirit or scope of the invention.

As will be evident to those skilled in the art, individual isomeric forms can be obtained by separation of mixtures thereof in conventional manner. For example, in the case of diastereoisomeric isomers, chromatographic separation may be employed.

Compound names were generated with ACD version 12.0; and Intermediates and reagent names used in the examples were generated with softwares such as Chem Bio Draw Ultra version 12.0, ACD version 12.0 or Auto Nom 2000 from MDL ISIS Draw 2.5 SP1.

In general, characterization of the compounds is performed according to the following methods: NMR spectra are recorded on 300 and/or 600 MHz Varian and acquired at room temperature. Chemical shifts are given in ppm referenced either to internal TMS or to the solvent signal.

All the reagents, solvents, catalysts for which the synthesis is not described are purchased from chemical vendors such as Sigma Aldrich, Fluka, Bio-Blocks, Combi-blocks, TCI, VWR, Lancaster, Oakwood, Trans World Chemical, Alfa, Fisher, Maybridge, Frontier, Matrix, Ukrorgsynth, Toronto, Ryan Scientific, SiliCycle, Anaspec, Syn Chem, Chem-Impex, MIC-scientific, Ltd; however some known intermediates, were prepared according to published procedures.

Usually the compounds of the invention were purified by column chromatography (Auto-column) on an Teledyne-ISCO CombiFlash with a silica column, unless noted otherwise.

The following abbreviations are used in the examples:

| | |
|---|---|
| EtOAc | ethyl acetate |
| TLC | thin layer chromatography |
| $K_2CO_3$ | potassium carbonate |
| $MgSO_4$ | magnesium sulfate |
| $CD_3OD$ | deuterated methanol |
| $CH_2Cl_2$ | dichloromethane |
| $Et_3N$ | trietheylamine |
| PPAA | propyl phosphonic anhydride |
| RT | room temperature |
| DMF | dimethylformamide |
| $NaHCO_3$ | sodium bicarbonate |

The following synthetic schemes illustrate how compounds according to the invention can be made. Those skilled in the art will be routinely able to modify and/or adapt the following schemes to synthesize any compound of the invention.

Example 1

Compound 1

N-(4-bromophenyl)-2-(4-ethyl-4-isopropyl-2,5-dioxoimidazolidin-1-yl)acetamide

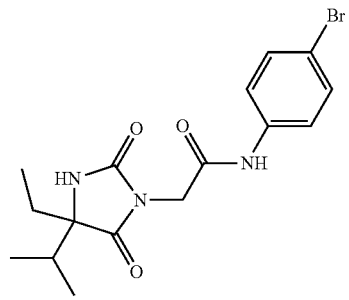 [SMILES: CCC1(C(C)C)NC(=O)N(CC(=O)Nc2ccc(Br)cc2)C1=O]

A mixture of 5-Ethyl-5-(1-methylethyl)-2,4-imidazolidinedione, (CAS #98492-91-2 (50 mg, 0.29 mmol), N-(4-bromophenyl)-2-chloro-acetamide (CAS #2564-02-5) (80 mg, 0.32 mmol), $K_2CO_3$ (48 mg, 0.35 mmol) in acetone was stirred at ambient temperature for 18 h. The mixture was extracted with EtOAc, the organic layer was washed with brine, dried over $MgSO_4$, filtered and solvent removed. The crude product was purified by preparative TLC. The title compound was isolated as white solid.

$^1$HNMR (CD$_3$OD): δ 0.86-1.05 (m, 9H), 1.77-1.87 (m, 2H), 1.96-2.06 (m, 1H), 4.27 (s, 2H), 7.41 (d, J=9.0 Hz, 2H), 7.48 (d, J=9.0 Hz, 2H).

Compounds 2 through 6 were prepared from the corresponding intermediate in a similar manner to the procedure described in Example 1 for Compound 1. The starting materials used and the compound's characteristics are described below in Table 1.

TABLE 1

| Comp. No. | IUPAC name | Starting material | $^1$H NMR δ (ppm) for compound |
|---|---|---|---|
| 2 | N-(4-bromophenyl)-2-(1,3-dioxotetrahydro-1H-pyrrolo[1,2-c]imidazol-2(3H)-yl)acetamide | 1H-Pyrrolo[1,2-c]imidazole-1,3(2H)-dione, tetrahydro- CAS # 5768-79-6 | $^1$HNMR (CD$_3$OD): δ 1.75-1.90 (m, 1H), 2.10-2.30 (m, 3H), 3.25-3.29 (m, 1H), 3.60-3.70 (m, 1H), 4.26 (s, 2H), 4.24-4.30 (m, 1H), 7.43 (d, J = 9.0 Hz, 2H), 7.48 (d, J = 9.0 Hz, 2H). |
| 3 | N-(4-bromophenyl)-2-(1,3-dioxohexahydroimidazo[1,5-a]pyridin-2(3H)-yl)acetamide | Imidazo[1,5-a]pyridine-1,3(2H,5H)-dione, tetrahydro- CAS # 4705-52-6 | $^1$HNMR (CD$_3$OD): δ 1.40-1.70 (m, 3H), 1.75 (d, J = 9.0 Hz, 1H), 1.90-2.05 (m, 1H), 2.10-2.20 (m, 1H), 2.93 (td, J = 13.0, 3.5 Hz, 1H), 3.95-4.15 (m, 2H), 4.29 (s, 2H), 7.43 (d, J = 9.0 Hz, 2H), 7.48 (d, J = 9.0 Hz, 2H). |
| 4 | N-(4-Bromophenyl)-2-(4,4-diethyl-2,5-dioxoimidazolidin-1-yl)propanide | 5,5-diethylimidazolidine-2,4-dione CAS # 5455-34-5 N-(4-bromophenyl)-2-chloro-propanamide CAS # 21262-08-8 | $^1$HNMR (CD$_3$OD): δ 0.88 (t, J = 7.4 Hz, 3H), 0.91 (t, J = 7.4 Hz, 3H), 1.55-1.65 (m, 2H), 1.69 (d, J = 7.4 Hz, 3H), 1.70-1.90 (m, 3H), 7.43 (d, J = 7.5 Hz, 2H), 7.48 (d, J = 7.5 Hz, 2H). |
| 5 | N-(4-Bromophenyl)-2-(4-methoxymethyl)-4-methyl-2,5-dioxoimidazolidin-1-yl)acetamide | 5-(methoxymethyl)-5-methyl-2,4-Imidazolidinedione CAS # 88807-85-6 N-(4-bromophenyl)-2-chloro-acetamide CAS # 2564-02-5 | $^1$HNMR (CD$_3$OD): δ 1.39 (s, 3H), 3.31 (s, 3H), 3.45 (d, J = 9.9 Hz, 1H), 3.61 (d, J = 9.9 Hz, 1H), 4.26 (s, 2H), 7.43 (d, J = 7.5 Hz, 2H), 7.48 (d, J = 7.5 Hz, 2H). |

TABLE 1-continued

| Comp. No. | IUPAC name | Starting material | $^1$H NMR δ (ppm) for compound |
|---|---|---|---|
| 6 | N-(4-Bromophenyl)-2-(6,8-dioxo-5,7-diazaspiro[3.4]octan-7-yl)acetamide 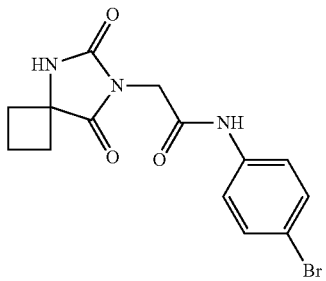 | 5,7-Diazaspiro[3.4]octane-6,8-dione CAS # 89691-88-3 N-(4-bromophenyl)-2-chloro-acetamide CAS # 2564-02-5 | $^1$HNMR (CD$_3$OD): δ 1.80-1.95 (m, 1H), 2.00-2.15 (m, 1H), 2.31-2.60 (m, 4H), 4.26 (s, 2H), 7.43 (d, J = 7.5 Hz, 2H), 7.48 (d, J = 7.5 Hz, 2H). |

Example 2

Compound 7

N-(4-Bromophenyl)-2-(4,4-dimethyl-2,5-dioxoimidazolidin-1-yl)propanamide

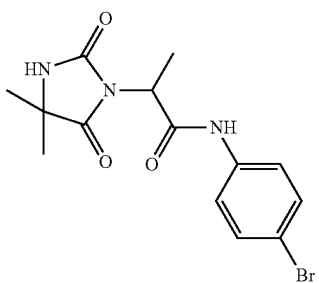 [SMILES: CC(C(=O)Nc1ccc(Br)cc1)N1C(=O)NC(C)(C)C1=O]

To a mixture of 2-(4,4-dimethyl-2,5-dioxoimidazolodin-1-yl)propanoic acid CAS#876709-28-3 (130 mg, 0.65 mmol), CH$_2$Cl$_2$ (3 mL), Et$_3$N (645 mg, 6.5 mmol), 4-Bromoaniline (60 mg, 0.65 mmol) was added PPAA (50% solution in DMF, 0.6 mL, 1.09 mmol). The mixture was stirred for 18 h at RT. The reaction was diluted with EtOAc washed with aq. NaHCO$_3$ (1N solution), dried with MgSO$_4$ and solvent removed. The crude mixture was purified by silicagel chromatography. The title compound was isolated as a white solid.

$^1$HNMR (CD$_3$OD): δ 1.33 (d, J=7.03 Hz, 3H), 1.80 (s, 3H), 1.82 (s, 3H), 3.95 (q, J=7.03 Hz, 1H), 7.36 (br s, 4H).

Example 3

Biological Data

Biological activity of compounds according to Formula I is set forth in Table 2 below. CHO-Ga16 cells stably expressing FPR2 were cultured in (F12, 10% FBS, 1% PSA, 400 μg/ml geneticin and 50 μg/ml hygromycin) and HEK-Gqi5 cells stable expressing FPR2 were cultured in (DMEM high glucose, 10% FBS, 1% PSA, 400 μg/ml geneticin and 50 μg/ml hygromycin). In general, the day before the experiment, 18,000 cells/well were placed in a 384-well clear bottom poly-d-lysine coated plate. The following day the screening compound-induced calcium activity was assayed on the FLIPR$^{Tetra}$. The drug plates were prepared in 384-well microplates using the EP3 and the MultiPROBE robotic liquid handling systems. Compounds were tested at concentrations ranging from 0.61 to 10,000 nM. Results are expressed as EC$_{50}$ (nM) and efficacy values.

TABLE 2

| Compound IUPAC name | FPR2 Gal6-CHO EC$_{50}$ (0.% eff) |
|---|---|
| N-(4-bromophenyl)-2-(1,3-dioxotetrahydro-1H-pyrrolo[1,2-c]imidazol-2(3H)-yl)acetamide | 343 nM (0.93) |
| N-(4-bromophenyl)-2-(4-ethyl-4-isopropyl-2,5-dioxoimidazolidin-1-yl)acetamide | 56 nM (0.99) |
| N-(4-bromophenyl)-2-(1,3-dioxohexahydroimidazo[1,5-a]pyridin-2(3H)-yl)acetamide | 243 nM (1.0) |
| N-(4-Bromophenyl)-2-(4-methoxymethyl)-4-methyl-2,5-dioxoimidazolidin-1-yl)acetamide | 306 nM (1.00) |
| N-(4-Bromophenyl)-2-(6,8-dioxo-5,7-diazaspiro[3.4]octan-7-yl)acetamide | 647 nM (1.00) |

What is claimed is:

1. A compound having Formula I or a pharmaceutically acceptable salt thereof or the individual enantiomers, diastereoisomers, zwitterions, tautomers or pharmaceutically acceptable salts thereof:

Formula I

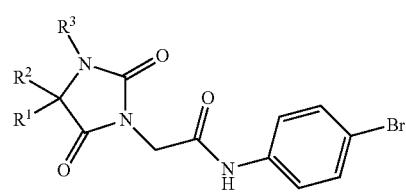

wherein:

R$^1$ is hydrogen, halogen, substituted or unsubstituted C$_{1-6}$ alkyl, substituted or unsubstituted C$_{2-6}$ alkenyl, substituted or unsubstituted C$_{2-6}$ alkynyl, substituted or unsubstituted C$_{3-8}$ cycloalkyl, substituted or unsubstituted $C_{3-8}$ cycloalkenyl substituted or unsubstituted heterocycle or substituted or unsubstituted $C_{6-10}$ aryl, or together with $R^2$ can form an optionally substituted cyclobutyl or cyclopropyl;

$R^2$ is isopropyl or together with $R^3$ can form a substituted or unsubstituted 3 to 6 member ring heterocycle or together with $R^1$ can form an optionally substituted cyclobutyl or cyclopropyl;

$R^3$ is hydrogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted $C_{3-8}$ cycloalkyl, substituted or unsubstituted $C_{3-8}$ cycloalkenyl, substituted or unsubstituted heterocycle, substituted or unsubstituted $C_{6-10}$ aryl or together with $R^2$ can form a substituted or unsubstituted 3 to 6 member ring heterocycle; and compounds N-(4-Bromophenyl)-2-(4,4-diethyl-2,5-dioxoimidazolidin-1-yl)propanamide;

N-(4-Bromophenyl)-2-(4-methoxymethyl)-4-methyl-2,5-dioxoimidazolidin-1-yl)acetamide; and N-(4-Bromophenyl)-2-(4,4-dimethyl-2,5-dioxoimidazolidin-1-yl)propanamide.

2. A compound according to claim 1 wherein:
$R^1$ is hydrogen, halogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted $C_{3-8}$ cycloalkyl, substituted or unsubstituted $C_{3-8}$ cycloalkenyl substituted or unsubstituted heterocycle or substituted or unsubstituted $C_{6-10}$ aryl; and
$R^2$ and $R^3$ form a substituted or unsubstituted 3 to 6 member ring heterocycle.

3. A compound according to claim 1, wherein:
$R^1$ is hydrogen; and,
$R^2$ and $R^3$ form a substituted or unsubstituted 3 to 6 member ring heterocycle.

4. A compound according to claim 1, wherein:
$R^1$ together with $R^2$ forms an optionally substituted cyclobutyl or cyclopropyl; and,
$R^3$ is hydrogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted $C_{3-8}$ cycloalkyl, substituted or unsubstituted $C_{3-8}$ cycloalkenyl, substituted or unsubstituted heterocycle, substituted or unsubstituted $C_{6-10}$ aryl.

5. A compound according to claim 1, wherein:
$R^1$ together with $R^2$ forms an optionally substituted cyclobutyl or cyclopropyl; and,
$R^3$ is H or substituted or unsubstituted $C_{1-6}$ alkyl.

6. A compound according to claim 1, wherein:
$R^1$ is hydrogen, halogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted $C_{3-8}$ cycloalkyl, substituted or unsubstituted $C_{3-8}$ cycloalkenyl substituted or unsubstituted heterocycle or substituted or unsubstituted $C_{6-10}$ aryl;
$R^2$ is isopropyl; and,
$R^3$ is hydrogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted $C_{3-8}$ cycloalkyl, substituted or unsubstituted $C_{3-8}$ cycloalkenyl, substituted or unsubstituted heterocycle, substituted or unsubstituted $C_{6-10}$ aryl.

7. A compound according to claim 1, wherein:
$R^1$ is substituted or unsubstituted $C_{1-6}$ alkyl;
$R^2$ is isopropyl; and,
$R^3$ is hydrogen.

8. A compound according to claim 1, selected from:
N-(4-bromophenyl)-2-(4-ethyl-4-isopropyl-2,5-dioxoimidazolidin-1-yl)acetamide;
N-(4-bromophenyl)-2-(1,3-dioxotetrahydro-1H-pyrrolo[1,2-c]imidazol-2(3H)-yl)acetamide;
N-(4-bromophenyl)-2-(1,3-dioxohexahydroimidazo[1,5-a]pyridin-2(3H)-yl)acetamide;
N-(4-Bromophenyl)-2-(4,4-diethyl-2,5-dioxoimidazolidin-1-yl)propanamide;
N-(4-Bromophenyl)-2-(4-methoxymethyl)-4-methyl-2,5-dioxoimidazolidin-1-yl)acetamide;
N-(4-Bromophenyl)-2-(6,8-dioxo-5,7-diazaspiro[3.4]octan-7-yl)acetamide; and
N-(4-Bromophenyl)-2-(4,4-dimethyl-2,5-dioxoimidazolidin-1-yl)propanamide.

9. A pharmaceutical composition comprising as active ingredient a therapeutically effective amount of a compound according to claim 1, and a pharmaceutically acceptable adjuvant, diluents or carrier.

10. A pharmaceutical composition according to claim 9, wherein the compound is selected from:
N-(4-bromophenyl)-2-(4-ethyl-4-isopropyl-2,5-dioxoimidazolidin-1-yl)acetamide;
N-(4-bromophenyl)-2-(1,3-dioxotetrahydro-1H-pyrrolo[1,2-c]imidazol-2(3H)-yl)acetamide;
N-(4-bromophenyl)-2-(1,3-dioxohexahydroimidazo[1,5-a]pyridin-2(3H)-yl)acetamide;
N-(4-Bromophenyl)-2-(4,4-diethyl-2,5-dioxoimidazolidin-1-yl)propanamide;
N-(4-Bromophenyl)-2-(4-methoxymethyl)-4-methyl-2,5-dioxoimidazolidin-1-yl)acetamide;
N-(4-Bromophenyl)-2-(6,8-dioxo-5,7-diazaspiro[3.4]octan-7-yl)acetamide; and,
N-(4-Bromophenyl)-2-(4,4-dimethyl-2,5-dioxoimidazolidin-1-yl)propanamide.

11. A method of treating a disorder associated with N-formyl peptide receptor 2 modulation, which comprises administering to a mammal in need thereof, a pharmaceutical composition comprising a therapeutically effective amount of at least one compound of Formula I

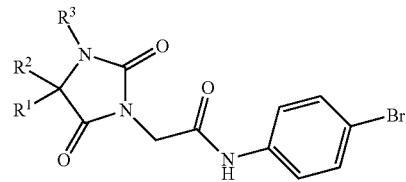

Formula I wherein:
$R^1$ is hydrogen, halogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted $C_{3-8}$ cycloalkyl, substituted or unsubstituted $C_{3-8}$ cycloalkenyl substituted or unsubstituted heterocycle or substituted or unsubstituted $C_{6-10}$ aryl, or together with $R^2$ can form an optionally substituted cyclobutyl;

$R^2$ is isopropyl or together with $R^3$ can form a substituted or unsubstituted 3 to 6 member ring heterocycle or together with $R^1$ can form an optionally substituted cyclobutyl or cyclopropyl;

$R^3$ is hydrogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted $C_{3-8}$ cycloalkyl, substituted or unsubstituted $C_{3-8}$ cycloalkenyl, substituted or unsubstituted heterocycle, substituted or unsubstituted $C_{6-10}$ aryl or together with $R^2$ can form a substituted or unsubstituted 3 to 6 member ring heterocycle; and compounds

- N-(4-Bromophenyl)-2-(4,4-diethyl-2,5-dioxoimidazolidin-1-yl)propanamide;
- N-(4-Bromophenyl)-2-(4-methoxymethyl)-4-methyl-2,5-dioxoimidazolidin-1-yl)acetamide; and,
- N-(4-Bromophenyl)-2-(4,4-dimethyl-2,5-dioxoimidazolidin-1-yl)propanamide.

12. The method of claim 11, wherein said compound is selected from:

- N-(4-bromophenyl)-2-(4-ethyl-4-isopropyl-2,5-dioxoimidazolidin-1-yl)acetamide;
- N-(4-bromophenyl)-2-(1,3-dioxotetrahydro-1H-pyrrolo[1,2-c]imidazol-2(3H)-yl)acetamide;
- N-(4-bromophenyl)-2-(1,3-dioxohexahydroimidazo[1,5-a]pyridin-2(3H)-yl)acetamide;
- N-(4-Bromophenyl)-2-(4,4-diethyl-2,5-dioxoimidazolidin-1-yl)propanamide;
- N-(4-Bromophenyl)-2-(4-methoxymethyl)-4-methyl-2,5-dioxoimidazolidin-1-yl)acetamide;
- N-(4-Bromophenyl)-2-(6,8-dioxo-5,7-diazaspiro[3.4]octan-7-yl)acetamide; and,
- N-(4-Bromophenyl)-2-(4,4-dimethyl-2,5-dioxoimidazolidin-1-yl)propanamide.

13. The method of claim 11, wherein the disorder associated with N-formyl peptide receptor 2 modulation is selected from ocular inflammatory diseases selected from: wet age-related macular degeneration, dry age-related macular degeneration, uveitis, dry eye, Keratitis, non-exudative age related macular degeneration, exudative age related macular degeneration, choroidal neovascularization, retinopathy of prematurity, acute macular neuroretinopathy, central serous chorioretinopathy, cystoid macular edema, diabetic macular edema, infectious keratitis, and post-surgery corneal wound healing.

14. The method of claim 11, wherein the mammal is a human.

* * * * *

UNITED STATES PATENT AND TRADEMARK OFFICE
CERTIFICATE OF CORRECTION

PATENT NO. : 8,729,096 B2
APPLICATION NO. : 13/765527
DATED : May 20, 2014
INVENTOR(S) : Richard L. Beard et al.

It is certified that error appears in the above-identified patent and that said Letters Patent is hereby corrected as shown below:

In the Specification

Column 1, line 36, delete "glucocotricoid" and insert -- glucocorticoid --, therefor.

Column 4, line 5, delete "—$O_{2-6}$" and insert -- —$C_{2-6}$ --, therefor.

Column 4, line 12, delete "—$SO_{1-6}$" and insert -- —$SC_{1-6}$ --, therefor.

Column 4, line 14, delete "—$O_{2-6}$" and insert -- —$C_{2-6}$ --, therefor.

Column 4, line 55, delete "Rx" and insert -- $R^x$ --, therefor.

Column 6, line 2, delete "Stahal&" and insert -- Stahl & --, therefor.

Column 6, line 3, delete "Chemica" and insert -- Chimica --, therefor.

Column 6, line 13, delete "Chemica" and insert -- Chimica --, therefor.

Column 7, line 14, delete "(PONS)" and insert -- (POHS) --, therefor.

Column 8, line 32, delete "(PONS)" and insert -- (POHS) --, therefor.

Column 9, line 55, delete "(PONS)" and insert -- (POHS) --, therefor.

Column 13, line 43, delete "diasteroisomeric" and insert -- diastereoisomeric --, therefor.

Column 14, line 12, delete "trietheylamine" and insert -- triethylamine --, therefor.

Signed and Sealed this
Fourteenth Day of October, 2014

Michelle K. Lee
*Deputy Director of the United States Patent and Trademark Office*